United States Patent
Calbet Benach

(10) Patent No.: US 7,313,446 B2
(45) Date of Patent: Dec. 25, 2007

(54) ELECTRODE ASSEMBLY FOR ELECTROTHERAPY DEVICES

(75) Inventor: José Calbet Benach, Barcelona (ES)

(73) Assignee: Indiba, S.A., Barcelona (ES)

( * ) Notice: Subject to any disclaimer, the term of this patent is extended or adjusted under 35 U.S.C. 154(b) by 324 days.

(21) Appl. No.: 10/433,528

(22) PCT Filed: Sep. 17, 2002

(86) PCT No.: PCT/ES02/00435

§ 371 (c)(1),
(2), (4) Date: Dec. 3, 2003

(87) PCT Pub. No.: WO03/024524

PCT Pub. Date: Mar. 27, 2003

(65) Prior Publication Data

US 2004/0082987 A1    Apr. 29, 2004

(30) Foreign Application Priority Data

Sep. 21, 2001 (ES) ............................. 200102327 U
Sep. 13, 2002 (ES) ............................. 200202227 U

(51) Int. Cl.
*A61N 1/04* (2006.01)

(52) U.S. Cl. ..................................... 607/150; 607/115

(58) Field of Classification Search ................ 607/115, 607/142, 145, 147, 148–150
See application file for complete search history.

(56) References Cited

U.S. PATENT DOCUMENTS

| | | | | |
|---|---|---|---|---|
| 4,883,457 A | * | 11/1989 | Sibalis | 604/20 |
| 5,601,618 A | * | 2/1997 | James | 607/71 |
| 6,728,577 B2 | * | 4/2004 | Minogue et al. | 607/48 |
| 2001/0027270 A1 | * | 10/2001 | Stratbucker | 600/382 |
| 2002/0107543 A1 | * | 8/2002 | Voznesensky et al | 607/3 |

FOREIGN PATENT DOCUMENTS

| | | |
|---|---|---|
| EP | 0 480 639 | 4/1992 |
| ES | 1 008 193 | 3/1989 |
| ES | 1 050 231 | 3/2002 |
| GB | 2160427 A * | 12/1995 |

* cited by examiner

*Primary Examiner*—George R. Evanisko
(74) *Attorney, Agent, or Firm*—Merchant & Gould P.C.

(57) ABSTRACT

The invention relates to an electrode assembly for electrotherapy devices. The assembly has at least one stainless steel metallic electrode and at least one electrode which is also metallic and which is covered with an insulating layer. Both of said electrodes are removably and electrically connected to a handle support in such a way that they can be actuated individually or together. The active surface area of said electrode assembly is provided with a configuration which adapts to that of the area of the patient's body to be treated. Depending on the therapy being followed, the active face of the electrodes may be static on the area of the patient to be treated or moved in order to massage said area.

10 Claims, 2 Drawing Sheets

ELECTRODE ASSEMBLY FOR ELECTROTHERAPY DEVICES

These apparatuses are mainly designed for the treatment of body parts being affected by neoplasias and other phenomena being caused by an abnormal cell growth and several other disorders.

Said apparatuses comprise an electronic recovery unit to which insulated, metallic electrodes and noninsulated metallic electrodes being preferably made of stainless steel are connected which are used independently.

These electrotherapy apparatuses are based on the application of high-frequency currents and are directed to producing hyperthermia effects, i.e. a local heating into the depth of the cellular tissues of given body parts being affected by the disorders.

The methods to obtain the hyperthermia with the aforementioned electrodes are: the capacitive approach by using the insulated, metallic electrodes, and the resistive approach by using the noninsulated electrodes being preferably made of stainless steel.

The treatments on the patient have been carried out so far by effecting the therapy with one of the electrodes and then with the other one.

This invention has as its object an electrode assembly by means of which a method is obtained which gives better results.

The invention is for such a purpose characterized in that the electrode assembly is made up of two coplanar electrodes one of which is made of stainless steel whereas the other one is also metallic and is besides provided with an insulating coating. These two electrodes are fitted and electrically connected to a carrier with handle thus allowing to simultaneously carry out both therapies hence generally resulting in more benefits being obtained in less application time.

The two electrodes are apt to removably and independently be fitted to the carrier with handle thus allowing to clean them and to use only one of them at the user's discretion.

The electrical connection of the electrodes to the carrier with handle and of this latter to the radio-frequency outputs of the hyperthermia recovery unit will be independent, that is to say that by disconnecting one of the electrodes it will be possible to use the other one without having to remove the one not being used from the carrier with handle.

This invention provides this electrode assembly with complementary features allowing to better adapt it to the therapy to be carried out in the different zones of a patient's body, and to better apply it as per the treatment to be followed.

According to this invention the effective surface of the electrode assembly will for such a purpose have a flat, concave or convex configuration as per the configuration of the zone to be treated, said effective surface conforming to said zone.

Also according to this invention the effective proportion of the surface of the capacitive electrode and of the resistive electrode will furthermore be the same or different in accordance with the therapy or treatment to be followed.

The application of this electrode assembly on the zone to be treated will besides according to the invention be effected in a stationary manner, i.e. without moving it, or else with a shifting motion by massaging said zone, in this latter case after having previously applied a moisturizing cream on the zone to be treated.

These and other characteristics will be best made apparent by the following detailed description whose understanding will be made easier by the accompanying two sheets of drawings showing practical embodiments being cited only by way of example not limiting the scope of the present invention.

Figure 4:
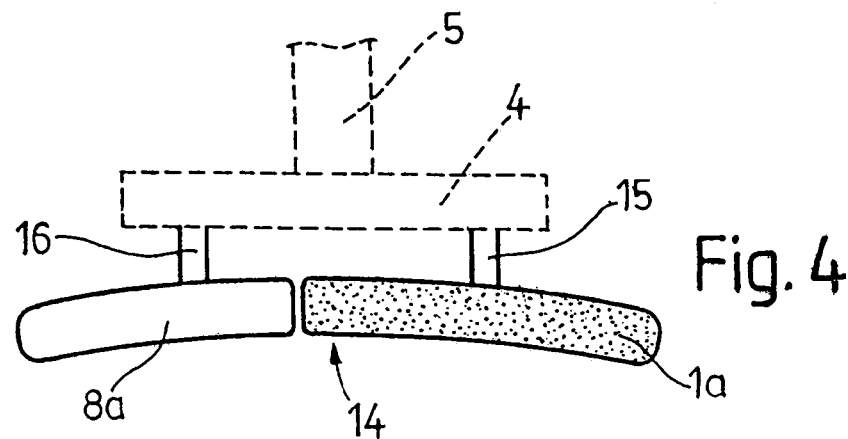
Figure 5:
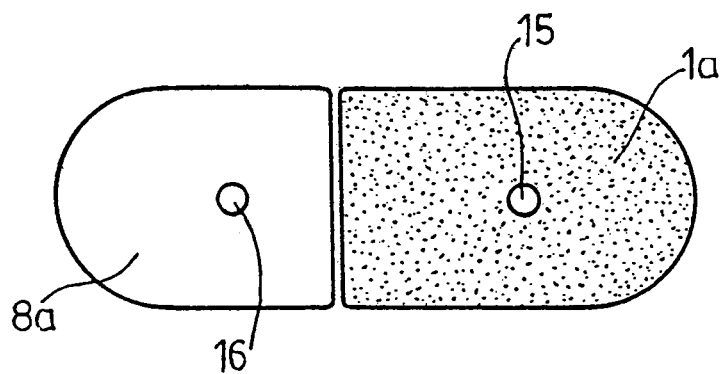
Figure 6:
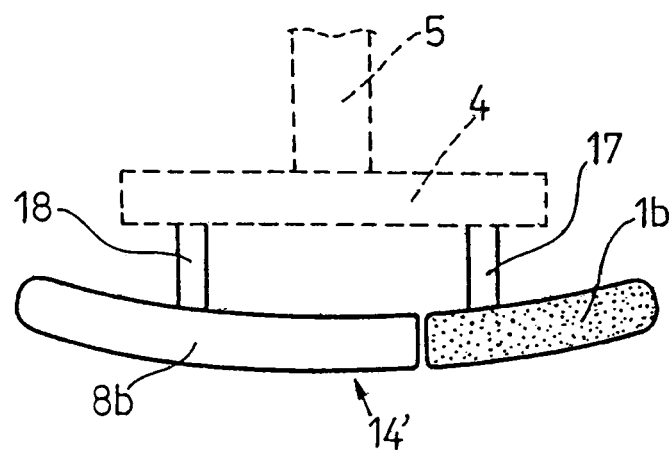
Figure 7:
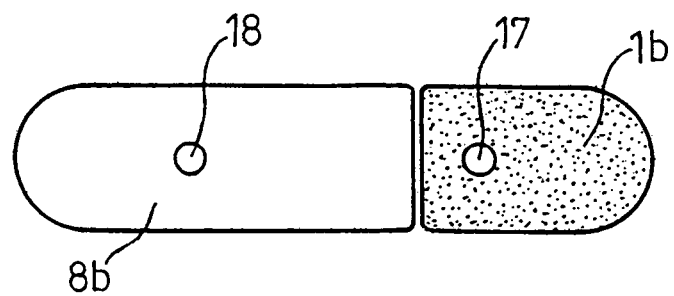

FIGS. 4 and 5 in an elevational and in a plan view diagrammatically show the electrode assembly having a concavely shaped effective surface; and FIGS. 6 and 7 also in an elevational and in a plan view diagrammatically illustrate said electrode assembly having a convexly shaped effective surface.

Figure 1:
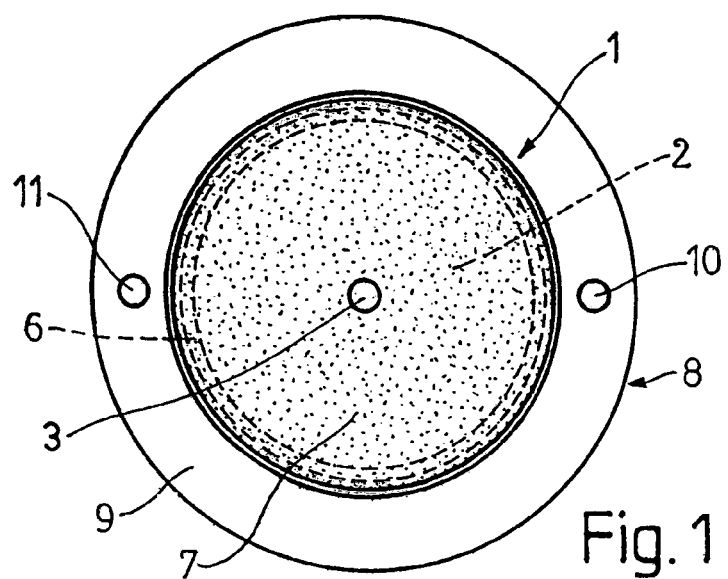
FIG. 1 shows in a plan-view an embodiment of the electrode assembly being the object of the invention.
Figure 2:
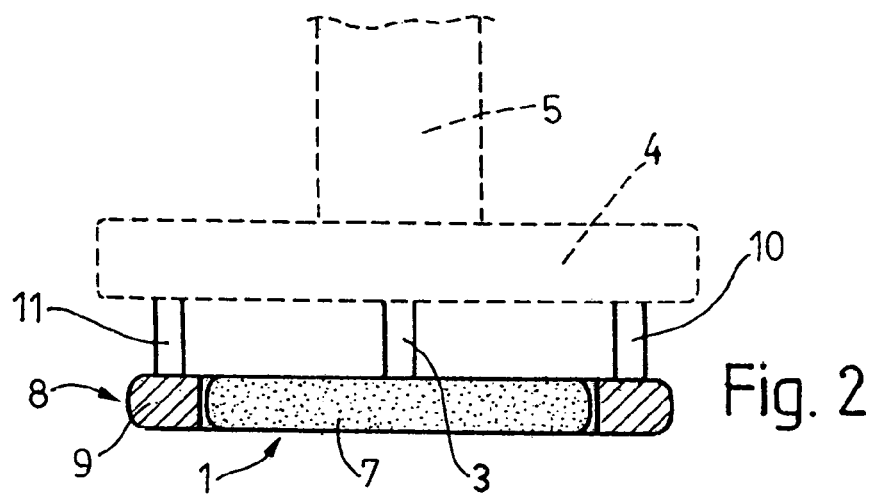
FIG. 2 illustrates this electrode assembly in a sectional elevation.

According to FIGS. 1 and 2 the electrode assembly comprises a (capacitive), circular electrode (1) being formed by a metallic disk (2) being provided at its center with a metallic pin (3) through which it is fitted and electrically connected to a carrier (4) with handle (5). The metallic disk is provided at its periphery with a shielding (6) being made of an adequate, electrically insulating, heat-resistant material, and is also provided with an insulating coating (7) covering the whole disk (2).

Around said capacitive electrode (1) and in a coplanar relationship with it the resistive electrode (8) is arranged and is formed by a stainless steel ring (9) being provided with two diametrically opposed, metallic pins (10) and (11) being apt to allow to fit and electrically connect this electrode to the carrier (4) with handle (5).

The therapeutic treatment can be jointly carried out with the two electrodes (1) and (8), i.e. with the capacitive and the resistive one, or else with only one of them by disconnecting or removing the electrode not being used from the carrier with handle.

Figure 3:
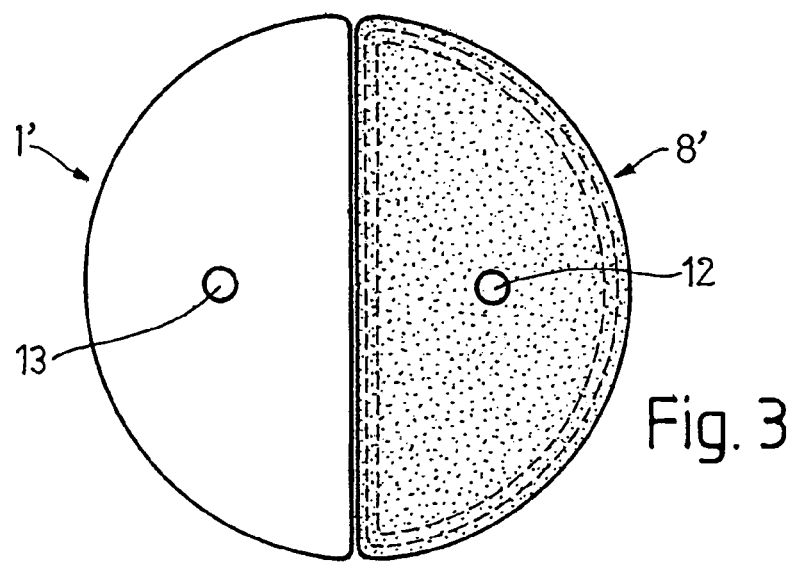
FIG. 3 represents another embodiment of the electrode assembly.

In FIG. 3 said electrodes (1') and (8') are semicircular thus forming a disk-shaped assembly, and each of them is respectively provided with a pin (12) and (13) allowing to fit and connect them to the corresponding carrier with handle.

According to FIGS. 4 and 5 the electrode assembly has an oblong configuration with radiused ends and a concavely shaped effective surface (14), a larger proportion pertaining to the metallic (capacitive) electrode (1*a*) being provided with an insulating coating as compared with the metallic (resistive) electrode (8*a*), said electrode assembly being for example apt to be applied on the head, knee, shoulder and other body parts.

In FIGS. 6 and 7 the electrode assembly has an oblong and longer configuration with radiused ends and a convexly shaped effective surface (14'), a smaller proportion pertaining to the capacitive electrode (1*b*) as compared with the resistive electrode (8*b*), said electrode assembly being for example apt to be applied on the axilla, the ham and other body parts.

Each of these electrodes has a metallic pin (15), (16), (17) and (18) through which it is removably fitted and electrically connected to the carrier (4) with handle (5).

The invention can within its essentiality be put into practice in other embodiments only in detail differing from those having been described above only by way of example, said other embodiments also falling within the protection being sought. This electrode assembly for electrotherapy apparatuses can hence be realized with the best suited means, components and accessories, the integrating members being replaceable with others being technically equivalent, all this being comprised within the scope of the appended claims.

The invention claimed is:

1. An electrode assembly for electrotherapy apparatuses comprising:
   a first metallic electrode having an effective surface adapted to contact the body,
   a second metallic electrode having an effective surface with an insulating coating thereon adapted to contact the body and configured to operate by a capacitive approach, the first and second electrodes being coplanar,
   a carrier releasably holding both electrodes, and
   a handle attached to the carrier,
   wherein the electrode assembly is configured to allow operation of each electrode individually or jointly.

2. An electrode assembly as per claim 1, wherein the two electrodes are removably and independently fitted to the carrier.

3. An electrode assembly as per claim 1, wherein the effective surfaces have a flat, concave or convex configuration for a configuration of a zone to be treated on the patient's body, the electrode assembly conforming to said zone.

4. An electrode assembly as per claim 1, wherein the effective surface of the first electrode is the same size as the effective surface of the second electrode.

5. An electrode assembly as per claim 1, wherein the effective surface of the first electrode is a different size than the effective surface of the second electrode.

6. An electrode assembly as per claim 1, wherein the effective surface of the first electrode is the same shape as the effective surface of the second electrode.

7. An electrode assembly as per claim 1, wherein the effective surface of the first electrode is a different shape than the effective surface of the second electrode.

8. An electrode assembly as per claim 1, wherein at least the first electrode comprises stainless steel.

9. A method of treating a patient's body, comprising:
   applying the electrode assembly of claim 1 to a zone to be treated on the patient's body, and
   holding the effective surfaces of the electrodes stationary on the tone to be treated.

10. A method of treating a patient's body, comprising:
    applying the electrode assembly of claim 1 to a zone to be treated on the patient's body, and
    shiftingly moving the effective surfaces of the electrodes on the zone to be treated.

* * * * *